United States Patent
MacDonald et al.

(10) Patent No.: US 8,562,954 B2
(45) Date of Patent: *Oct. 22, 2013

(54) DENTAL COMPOSITIONS WITH SENSITIVITY RELIEF

(75) Inventors: Jeff MacDonald, Pomona, CA (US); Robert Hayman, Los Angeles, CA (US)

(73) Assignee: Discus Dental, LLC, Culver City, CA (US)

( * ) Notice: Subject to any disclaimer, the term of this patent is extended or adjusted under 35 U.S.C. 154(b) by 959 days.

This patent is subject to a terminal disclaimer.

(21) Appl. No.: 11/927,252

(22) Filed: Oct. 29, 2007

(65) Prior Publication Data

US 2008/0112901 A1   May 15, 2008

Related U.S. Application Data

(63) Continuation of application No. 11/173,632, filed on Jun. 30, 2005.

(60) Provisional application No. 60/585,224, filed on Jul. 2, 2004.

(51) Int. Cl.
*A61K 8/00* (2006.01)
*A61K 8/21* (2006.01)
*A61K 8/24* (2006.01)
*A61Q 11/00* (2006.01)

(52) U.S. Cl.
USPC ............ 424/49; 424/401; 424/52; 424/57

(58) Field of Classification Search
USPC .............................. 424/49, 52, 57, 401
See application file for complete search history.

(56) References Cited

U.S. PATENT DOCUMENTS

| | | | |
|---|---|---|---|
| 767,553 A | 8/1904 | Edgelow | |
| 803,474 A | 8/1905 | Dennis | |
| 1,642,653 A | 9/1927 | Goldstein | |
| 1,691,785 A | 11/1928 | Remensynder | |
| 1,934,688 A | 11/1933 | Ackerman | |
| 2,257,709 A | 9/1941 | Anderson | |
| 2,798,053 A | 7/1957 | Brown | |
| 2,835,628 A | 5/1958 | Saffir | |
| 2,858,281 A | 10/1958 | Bauman et al. | |
| 3,175,951 A | 3/1965 | Tucker | |
| 3,863,006 A | 1/1975 | Hodosh | |
| 4,357,318 A | 11/1982 | Shah et al. | |
| 4,634,589 A | 1/1987 | Scheller | |
| 5,037,639 A | 8/1991 | Tung | |
| RE34,196 E | 3/1993 | Munro | |
| 5,211,939 A | 5/1993 | Turesky et al. | |
| 5,240,697 A | 8/1993 | Norfleet et al. | |
| 5,268,167 A | 12/1993 | Tung | |
| 5,270,031 A | 12/1993 | Lim | |
| 5,460,803 A | 10/1995 | Tung | |
| 5,503,823 A * | 4/1996 | Norfleet et al. ............ 424/52 |
| 5,534,244 A | 7/1996 | Tung | |
| 5,562,895 A | 10/1996 | Tung | |
| 5,589,159 A | 12/1996 | Markowitz et al. | |
| 5,645,428 A | 7/1997 | Yarborough | |
| 5,690,912 A | 11/1997 | Campbell | |
| 5,693,314 A | 12/1997 | Campbell et al. | |
| 5,713,738 A | 2/1998 | Yarborough | |
| 5,723,500 A * | 3/1998 | Stringer et al. ............ 514/736 |
| 5,735,942 A | 4/1998 | Litkowski et al. | |
| 5,849,267 A | 12/1998 | Collins et al. | |
| 5,851,512 A | 12/1998 | Fischer | |
| 5,858,332 A | 1/1999 | Jensen et al. | |
| 5,891,233 A | 4/1999 | Salonen et al. | |
| 5,932,192 A | 8/1999 | Campbell et al. | |
| 5,981,233 A | 11/1999 | Ringpfeil | |
| 6,000,341 A | 12/1999 | Tung | |
| 6,056,930 A | 5/2000 | Tung | |
| 6,306,370 B1 | 10/2001 | Jensen et al. | |
| 6,309,625 B1 | 10/2001 | Jensen et al. | |
| 6,361,320 B2 | 3/2002 | Yarborough | |
| 6,368,576 B1 | 4/2002 | Jensen et al. | |
| 6,416,745 B1 | 7/2002 | Markowitz et al. | |
| 2003/0124067 A1 | 7/2003 | Yue et al. | |
| 2004/0022747 A1 | 2/2004 | Fisher et al. | |
| 2004/0115140 A1* | 6/2004 | Joziak et al. ............ 424/52 |
| 2006/0013778 A1 | 1/2006 | Hodosh | |

FOREIGN PATENT DOCUMENTS

| | | |
|---|---|---|
| DE | 1566227 | 10/1969 |
| DE | 1489712 | 4/1980 |
| DE | 2848237 | 5/1980 |
| EP | 0325267 | 5/1994 |
| EP | 0286776 | 10/1998 |
| WO | WO 00/28953 | 5/2000 |
| WO | WO 2004/075770 | 9/2004 |

OTHER PUBLICATIONS

J. R. Simplot Company, Material Safety Data Sheet (Potassium Nitrate), Jun. 2001 (internet).
Comenius—European Cooperation on School Education, Chemical Safety Data: Sodium Fluoride, Apr. 2005 (internet).

* cited by examiner

Primary Examiner — Lezah Roberts

(57) ABSTRACT

A one-component prescription fluoride treatment composition having both fluoride efficacy and sensitivity relief is disclosed. The composition includes at least one metal fluoride and a nerve desensitizing agent such as potassium nitrate. The invention further includes a composition having at least one metal fluoride less than about 1.15% by weight of at least one metal fluoride; less than about 5 percent by weight of at least one alkali metal salt having desensitizing effect; at least one carrier; and at least one foaming agent that has thickening property. The composition may be formulated into a gel, a paste or any other convenient form, some of which contain abrasives.

20 Claims, No Drawings

DENTAL COMPOSITIONS WITH SENSITIVITY RELIEF

CROSS-REFERENCE TO RELATED APPLICATIONS

This application is a continuation of U.S. patent application Ser. No. 11/173,632 filed on Jun. 30, 2005, which claims the benefit of U.S. provisional patent applications Ser. No. 60/585,224, filed Jul. 2, 2004, entitled "Sensitivity Relief Gel", the contents of which is incorporated herein by reference.

FIELD OF THE INVENTION

The present invention relates to improvements in tooth treatment compositions. In particular, this invention relates to compositions suitable for both fluoride treatment and sensitivity relief.

BACKGROUND OF THE INVENTION

Many attempts have been made to provide dentinal sensitivity relief. Stannous ion has been linked to treatment of dentine hypersensitivity. U.S. Pat. No. 5,690,912 teaches that in order for the stannous ion to be efficacious in treating dentine hypersensitivity, it must be stable and freely available and not in chemical combination with other ingredients. The patent discloses an oral hygiene preparation containing $SnF_2$ in combination with 87-97 percent by weight anhydrous glycerin and 2-10 percent by weight polyethylene glycol having an average molecular weight of 1000.

Besides $SnF_2$, other materials generally referred to as "nerve agents" or "nerve desensitizing agents" have been used in the treatment of hypersensitive teeth. Such agents reportedly reduce the excitability of the nerve in a sensitive tooth, and one of the most well-known agents used in commercial dentifrices for sensitive teeth for this purpose is potassium nitrate, and discussed in U.S. Pat. No. 3,863,006. Examples of other agents in this category include other potassium salts such as potassium bicarbonate, potassium chloride and the like, as well as sodium and lithium nitrates.

Another approach to controlling dentinal hypersensitivity is the use of agents to fully or partially occlude tubules. Examples of such "tubule blocking agents" include the following: charged polystyrene beads (U.S. Pat. No. 5,211,939); apatite (U.S. Pat. No. 4,634,589); a polyacrylic acid polymer having a typical molecular weight from about 450,000 to about 4,000,000 (U.S. Pat. No. 5,270,031); and certain clays (U.S. Pat. No. 5,589,159). Still others have attempted to treat dentin sensitivity by inducing the growth of minerals inside the dentinal tubules. A further approach (described in U.S. Pat. Nos. 5,735,942 and 5,891,233) is the use of bioactive glass to treat tooth sensitivity. In general, most of these inventions apparently suffer from problems of fluoride incompatibility and the abrasive nature of these inorganic solids can also be problematic.

The efficacy of fluoride in caries prophylaxis is well established, and topical application of aqueous solutions of various water-soluble fluorides is a rather routine procedure in dental offices and clinics. Toothpaste compositions having certain fluorides have been recognized as effective against caries by the American Dental Association. It is also known that certain metallic ions, for example, stannous fluoride ($SnF_2$), can have a significant effect on the anticariogenic efficacy of fluorides, and has been used in dentistry since the 1950's to treat various oral conditions. Also, in the 1950's, it was reported in scientific literature that the use of a source of stannous ions in conjunctions with fluoride gives a more effective anticariogenic product than is attained with fluoride alone (J. C. Muhler et al., J.A.D.A. 51, 665 (1955)). Topical application of $SnF_2$ has also consistently shown dramatic reductions in dental caries activity with minimal side effect as well as been indicated clinically to be efficacious in the reduction of dentinal hypersensitivity. This latter therapeutic effect is believed to be due, to a large extent, to the stannous ion ($Sn^{2+}$) component of the salt. More recently, relatively low concentrations of In(III) have been found to coact with fluorides to provide a high level of anticariogenic activity (U.S. Pat. No. 3,175,951, granted Mar. 30, 1965).

U.S. Pat. No. 5,693,314 teaches that attempts to include mixtures of a desensitizing agent such as $SnF_2$ with another desensitizing source such as potassium nitrate, in a single dentifrice composition are of limited effect. Additionally, prolonged contact between $Sn^{2+}$ and nitrate ion in a single dentifrice results in a reaction of these ions into potentially toxic materials. Thus, the solution is in keeping the two desensitizing sources separate from each other, and combining them for the first time only on the surface of the teeth to avoid any appreciable formation of insoluble tin or reaction product of tin.

U.S. Pat. No. 5,932,192 again teaches a two-component composition of stannous salt and potassium salt, to prevent the stannous compounds from reacting with water and other common oral care ingredients to form insoluble tin. Specific levels of water content within the potassium salt component (at least 44 percent by weight) and the overall water content (at least 22 percent by weight) are said to reduce the astringency, sourness and bitterness of the stannous salt.

U.S. Pat. No. 6,416,745 teaches dental compositions and methods for treating dentinal hypersensitivity based on anionic liposomes that are capable of inducing mineral formation in the dentinal tubules by partially or fully blocking them. The compositions of the liposomes and a suitable carrier are touted to be capable of delivering additional agents useful in the treatment of dentinal hypersensitivity by combining stannous fluoride directly with another desensitizing agent to further take advantage of the known anticariogenic and anti-microbial action of $SnF_2$.

Thus, it is clear that those skilled in the relevant art recognize that in order to capture the efficacy of stannous fluorides when additional desensitizing agents are added to an over-the-counter composition, either a 2-component system or agents such as liposomes are needed.

Therefore, there remains a need for a one-component composition having fluoride efficacy and sensitivity relief that a dental professional can easily administer to the teeth of patients during office visits.

SUMMARY OF THE INVENTION

The present invention relates to one-component prescription fluoride treatment compositions having both sensitivity relief and fluoride efficacy.

In one embodiment, a composition includes an effective amount of at least one source of fluoride for maximum efficacy, up to about 5 percent by weight of at least one alkali metal salt having desensitizing effect, and a carrier.

In another embodiment, a composition includes an effective amount of at least one source of fluoride for maximum efficacy; up to about 5 percent by weight of a mixture of at least one alkali metal salt having desensitizing effect and an amorphous calcium and/or strontium phosphate; and a carrier.

The present invention further relates to the use of foaming agents which when present in small quantities, may also act as thickening agents. Exemplary ones include a hydrophobic component and a hydrophilic component. The use of such foaming agents tends to decrease the amount of thickening agents normally used to formulate a dental paste, a dental gel, or any other thickened state, and thus reduces any unwanted effects that the thickeners might have on the efficacy of fluorides, and/or sensitivity relief.

In one aspect, optional additives including abrasives, thickeners, binders, additional carriers, surfactants, foaming agents, water, sweeteners, preservatives, vitamins, flavorings, coloring agents, anti-plaque agents, anti-staining compounds, pH adjusting agents or mixtures thereof may also be dispersed in the carrier, the amount or type depends on the physical form of the composition.

In another aspect, the compositions may be formulated in the form of tooth pastes, gels, dentifrices to be brushed or applied on the teeth, in the form of mouthwashes, or other delivery forms, to be prescribed and/or administered by a dental professional. Examples of alternative forms include a tooth powder, a buccal adhesive patch, an oral spray, any coating that may adhere to the oral cavity and the like.

The present invention together with the above and other advantages may best be understood from the following detailed description of the embodiments of the invention below.

DETAILED DESCRIPTION OF THE INVENTION

The detailed description set forth below is intended as a description of the presently exemplified compositions provided in accordance with aspects of the present invention and is not intended to represent the only forms in which the present invention may be prepared or utilized. It is to be understood, however, that the same or equivalent functions and components may be incorporated and these other embodiments are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein may be used in the practice or testing of the invention, the exemplified methods, devices and materials are now described.

Fluoride sources that are effective in treating dental caries include metal fluoride salts such as sodium fluoride, sodium monofluorophosphate, potassium fluoride, lithium fluoride, ammonium fluoride, stannous fluoride; zinc ammonium fluoride, tin ammonium fluoride, calcium fluoride and cobalt ammonium fluoride, and water soluble amine hydrofluorides. Generally, sodium fluoride and stannous fluoride are useful examples.

It is well recognized in the art that the efficacy of the fluoride treatment depends on the solubility of the fluoride compound, and the availability of fluoride ions, as the primary method of testing for fluoride efficacy in a clinical sense is to measure "total" and "available" fluoride. For example, the total fluoride of compositions of the present invention is at least about 5000 ppm, and more for example, the total fluoride of the composition is at least about 5300 ppm. The available fluoride ion is at least, for example, about 4900 ppm, more for example, about 5000 ppm.

Though acidic fluoride solutions are amongst the most effective ones in delivering fluoride ions, they also usually may lead to demineralization of the teeth. The pH of the composition is thus kept at about 5.5 or above, or better, to be kept between about 7 to about 8.5. The addition of some metal ions such as Indium III, however, have been shown to prevent demineralization at low pH by decreasing enamel solubility, thus its use may potentially expand the range of possible pH to be used.

In general, the ranges of pH may be achieved by including a pH adjusting agent in the composition. Exemplary adjusters may be those that do not interfere with the activity of fluorides and may include potassium hydroxide or hydrochloric acid. The less desired ones, though usable under some circumstances, are those that might impede or potentially impede fluoride activity, such as phosphates like tetrapotassium pyrophosophates, and nitrates.

The amount of the fluoride source used in the present invention for delivering the maximum efficacy is, for example, up to about 1.2 percent by weight, and more for example, up to about 1.15 percent by weight.

Suitable desensitizing agents may include alkali nitrates such as potassium nitrate, sodium nitrate and lithium nitrate; and other potassium salts such as potassium chloride and potassium bicarbonate. The most often used ones include potassium nitrate.

The percent of desensitizing agent may be present up to, for example, about 5 percent by weight, more for example, up to about 4 percent by weight, and even more for example, up to about 3 percent by weight. At these exemplary levels, the efficacy of the fluoride is not significantly impaired. However, when the amount present is significantly above 5%, some degradation of fluoride efficacy is observed.

The presence of additional metal salts, such as salts having desensitizing effects, is generally believed to inhibit the solubility of the fluoride salt and hence the efficacy of the fluoride treatment. Since the prescription type dental composition typically contains at least 3 to 4 times the amount of fluoride usually present in an over the counter tooth paste, it is reasonable to also believe that this higher level of efficacy will be severely compromised if other salts are present, thus defeating the purpose of having a higher concentration of fluoride in the first place. Based on the above, any salts that might impede or potentially impede fluoride activity, such as phosphates like tetrapotassium pyrophosophates, and nitrates, though not present in significant amounts to impart pH adjusting properties, are not generally recommended as pH adjusting agents, as discussed above.

Surprisingly, the present inventors have discovered that when the percent of desensitizing salts is present, for example, at less than about 5%, or any of the desirable amounts mentioned above, the fluoride efficacy is preserved or minimally affected.

Further, it is also surprising and contrary to prior teachings, that both the fluoride and the desensitizing agent may be formulated in a one-component composition without the presence of agents such as liposomes that are designed to keep the fluoride material apart from the desensitizing agent until the time of use.

In addition to the de-sensitizing agents mentioned above, amorphous calcium compounds such as amorphous calcium phosphate (ACP), amorphous calcium phosphate fluoride (ACPF) and amorphous calcium carbonate phosphate (ACCP) amorphous calcium carbonate phosphate (ACCP), amorphous calcium carbonate phosphate fluoride (ACCPF) or mixtures thereof may also be used. These agents may also re-mineralize teeth, collectively known herein as "amorphous calcium phosphates". These amorphous compounds are disclosed in U.S. Pat. Nos. 5,037,639, 5,268,167, 5,437,857, 5,562,895, 6,000,341, and 6,056,930, the disclosure of each is hereby incorporated by reference in its entirety.

In addition to amorphous calcium compounds, amorphous strontium compounds such as amorphous strontium phosphate (ASP), amorphous strontium phosphate fluoride (ASPF), amorphous strontium calcium phosphate (ASCP), amorphous strontium calcium carbonate phosphate (ASCCP), amorphous strontium carbonate phosphate fluoride (ASCPF), amorphous strontium calcium carbonate phosphate fluoride (ASCCPF) and mixtures thereof may also be used. These compounds are collectively "amorphous strontium phosphate" as used herein. In addition, these may also be used as re-mineralization agents, as noted above. These compounds are disclosed in U.S. Pat. No. 5,534,244, the content of which is hereby incorporated by reference in its entirety.

Some of the compounds above may also be used in fluoridating teeth. All of the above amorphous compounds or solutions which form the amorphous compounds, when applied either onto or into dental tissue prevent and/or repair dental weaknesses such as dental caries, exposed roots and dentin sensitivity.

The amorphous compounds are generally present separately, for example, a first component may include a source of phosphate and a second component may include a source of calcium or strontium. When the two components are mixed, the source of phosphate and the source of calcium, strontium or mixture may combine to form amorphous calcium phosphate, which when applied to teeth, may precipitate onto the surface of the teeth where it may be incorporated into hydroxyapatite, assisting in remineralization of the tooth enamel, as well as decreasing sensitivity, as noted above. The remineralization discussion can be found in U.S. Pat. Nos. 5,037,639, 5,268,167, 5,460,803, 5,534,244, 5,562,895, 6,000,341, and 6,056,930, noted above, and incorporated herein by reference.

Even though the source of calcium or strontium is kept separately from the source of phosphate, a separate container or compartment is not the only way to effect separation. Separation may also be effected by means of distance, or a partition which may involve encapsulating the source of calcium or strontium in one capsule, layer or an immobilized medium, generally referred to as a component, and the source of phosphate in another capsule, layer or an immobilized medium, also generally referred to as a component.

For example, the source of phosphate may includes monosodium phosphate ($NaH_2PO_4$), disodium phosphate, tetrapotassium pyrophosphate and thereof. As discussed above, the second component, for example, comprises a source of calcium or strontium, which combines with phosphate to form the various amorphous calcium and/or strontium phosphates.

The source of phosphate is, for example, present in an amount of from about 0.2 percent to about 2 percent by weight, further for example, between about 0.2 percent to about 1 percent by weight. These may be used alone or in combination with the other sensitivity relief agents such as nitrates mentioned above.

The source of calcium, strontium or combinations thereof in the second component, for example, may include a calcium salt, a strontium salt, and thereof, further for example, a calcium salt such as calcium nitrate, in an amount of from about 0.25 percent by weight to about 1.5 percent by weight, for example, about 0.3 percent to about 1 percent by weight.

In practice, it is practical to include as much phosphate as possible without impairing the activity of fluoride, as the phosphate salt may further act to adjust the pH of the composition, as noted above.

The carriers or humectants contemplated for use in the inventive compositions may include polyols, such as glycerol, sorbitol, polyethylene glycols, propylene glycols, hydrogenated partially hydrolyzed polysaccharides and the like. A single carrier or a combination of carriers is also contemplated. The carriers are generally present in amounts up to, for example, about 80 percent, more for example, from about 15 to about 70 percent, and even more for example, about 25 to about 60 percent by weight for toothpaste formulations.

The composition may also contain additional or optional ingredients, some of which are typically or suitably incorporated into oral health care compositions, depending on the form the composition takes. These ingredients include abrasives, thickeners, surfactants, foaming agents, binders, water, sweeteners, preservatives, vitamins, flavorings, coloring agents, ant-plaque agents, anti-staining compounds, pH adjusting agents and combinations thereof.

The additional or optional ingredients may be present to impart a particular function to the composition. For example, if it is desirable that the composition has an abrasive property, then abrasives are used. Suitable abrasives may include silicas and hydrates such as amorphous fumed silicas; alumina and hydrates thereof, such as alpha alumina trihydrate; silicates such as magnesium trisilicate, zirconium silicate, aluminosilicate such as calcined aluminum silicate and aluminum silicate; carbonates such as magnesium carbonate and calcium carbonate; polymethylmethacrylate; powdered polyethylene; silica xerogels, hydrogels and aerogels, and the like. Also suitable as abrasive agents are calcium pyrophosphate, insoluble sodium metaphosphate, dicalcium orthophosphate, particulate hydroxyapatite and the like. Depending on the form that the oral composition of the present invention is to take, such as a gel or a paste, the abrasive agent or agents may be present in an amount up to, for example, 30 percent by weight, more for example, from about 1 to about 25 percent by weight, even more for example, from about 10 to about 25 percent by weight, particularly when the composition is formulated into a toothpaste.

At the same time, thickeners may be added to the composition to form, for example, a paste or a gel. Some silicas mentioned above may also function as a thickener. Other thickeners may include carageenan, pectin, poloxamer, natural and synthetic waxes. When present, the thickener may be at a level, for example, from about 0.1 to about 20 percent by weight, more for example, from about 1 to about 15 percent by weight.

When abrasives are present to provide the composition with desired abrasiveness, the activity of fluoride ions is not generally impaired. Even though some of the abrasive materials, such as silicas, will also thicken the composition if present in larger quantities, a composition containing more silica may not require other thickeners or may need less of the other thickeners to produce a paste or gel. However, too much abrasive material, on the other hand, may not be desirable, not only because they may tend to impart excessive abrasiveness of the resulting composition, but also because an excessive amount of an abrasive material, especially silica, may tend to inhibit fluoride activity.

Foaming agents may also used in the composition. Especially useful foaming agents are those including both a hydrophilic component and a hydrophobic component, such as copolymers of ethylene oxide and propylene oxide. Hydrophobic components may be present in the foaming compounds, for example, from about 30 to about 40 percent by weight, more for example, from about 31 to about 38 percent by weight, and even more for example, from about 33 to about 36 percent by weight. Combinations of foaming agents having the above noted desirable characteristics may also be useful. Commercial examples may include Pluronic P84, available from BASF Corporation (North Mount Olive, N.J., USA).

Any material that can both thicken and provide another additional desired function in a composition will be greatly advantageous if it also does not impair the fluoride activity at the same time to any significant extend. Surprisingly, it is found that when a small amount of the exemplary foaming agent is added to the compositions of the present invention, it also provides a thickening effect, thus in effect reducing the amount of thickeners needed. Thus, it decreases any actual or potential fluoride impairment effect that might be caused by the use of some or excessive thickeners. This thickening effect is further enhanced when certain surfactants are also present.

Useful surfactants, such as soap, which may be anionic, nonionic, cationic, amphoteric and/or zwitterionic, may be present in amounts up to, for example, about 15 percent, more for example, about 0.1 to about 15 percent, even more for example, about 0.25 to about 10 percent by weight. Anionic and/or nonionic surfactants are especially useful. These useful surfactants include sodium lauryl sulfate, sodium lauroyl sarcosinate, sodium dodecylbenzene sulfonate and mixtures thereof, though others may also be used.

Binders may also be used in the compositions of the invention. Suitable ones may include carboxymethyl cellulose, carboxyethyl cellulose, polyvinylpyrrolidone, hydroxyethyl cellulose, and hydroxypropyl cellulose, as well as xanthan gums, Irish moss and gum tragacanth, carageenan, pectin and mixtures thereof. The binders may be present in the amount, for example, from about 0.01 to about 10 percent by weight, more for example, about 0.1 to about 2 percent by weight. Some binders may also act as thickeners and vice versa, although binders in general usually may impart other properties, such as, adhesiveness, ability to bind and hold other ingredients together. Once again, the chosen ones may include those that do not significantly impede the efficacy of fluoride.

Any artificial sweetener, including saccharin, is suitable for inclusion to impart a sweet taste if desired, and may be present at levels, for example, of about 0.1 to about 5 percent by weight, more for example, 0.2 to about 2 percent by weight.

In addition to sweeteners, flavorings normally used in dental formulation may be used and may include natural flavors like mint, and peppermint, artificial flavors like Tutti Fruitti, Grape, Cherry and others. Suitable flavors are usually included in low amounts, such as, for example, from about 0.01 to about 5 percent by weight, more for example, from about 0.1 to about 2 percent by weight.

Compositions in accordance with the present invention may, include antibacterial agents including, for example, phenolics and salicylamides, and sources of certain metal ions such as zinc, copper, silver and stannous ions, for example in salt form such as zinc, copper and stannous chloride, and silver nitrate. These are again present in small quantities when used.

Dyes/colorants suitable for oral health care compositions, i.e. FD & C Blue #1, FD & C Yellow #10, FD & C Red #40, etc., may be employed in the subject formulations as well, if a color composition is desired. Additional, preservatives such as benzoates and sorbates, vitamins such as vitamins C and E, anti-plaque agents such as copper salts, strontium salts and magnesium salts may also be included.

Anti-staining compounds such as silicone polymers, plant extracts and mixtures thereof may also be present.

Except where otherwise noted, references to toothpastes are to be construed as applying to gels as well, and mouthwashes include oral rinses and similar preparations. Mouthwashes may include ethanol at a level of, for example, from 0 to 60 percent, more for example, from 5 to 30 percent by weight.

A dentifrice composition in accordance with the present invention may be made by mixing the ingredients in any conventional manner, for example by creating a gel with the water and gelling agent prior to adding the water soluble ingredients. Next, a surfactant is added prior to the addition of the hydrophobic ingredients with blending. The mixture is then packaged in a conventional dentifrice container such as a tube. Compositions of the present invention are meant to be applied by a dental professional during an office visit, to the surface of the teeth through conventional brushing, coating, painting or other direct or indirect application technique.

While the present invention has been described, the instant invention will be further described with reference to the following non-limiting examples.

EXAMPLES

Test Method

Total Fluoride Determination:

The analysis for total fluoride of the toothpaste was performed under the procedure identified as Number 1 in the FDA Monograph with updated procedures. The test was performed in triplicate on fresh sample using direct potentiometry.

Complete dentifrice slurries in triplicates of 0.25 g samples were diluted to 25 ml with deionized water. The slurries were stirred for 20 minutes to assure uniform distribution. After diluting 1:1 with TISAB II (total ionic strength adjustment buffer), the solutions were analyzed for fluoride using a fluoride ion specific electrode and a digital pH meter. A standard fluoride curve was similarly prepared as a control.

Soluble Ionic Fluoride Determination:

The analysis for soluble ionic fluoride of the toothpaste was performed under the procedure identified as Number 29 in the FDA Monograph with updated procedures. The test was performed in triplicate on fresh and aged (90 days at 37° C.) samples using direct potentiometry. Intermediate analysis at 1:10 dilution were performed to monitor the progress of the stability testing.

Complete dentifrice in samples sizes of approximately 0.25 g, 2.5 g, and 4 g of each dentifrice samples were slurried with 25 ml (or 12 ml for 1:3) deionized water (1:100, 1:10, and 1:3 dilution) for exactly 5 minutes. The slurries were then immediately centrifuged for 10 minutes at 10,000 rpm. One (1) ml of each supernatant was added to 1 ml of TISAB II. The solutions were analyzed for fluoride using a fluoride ion specific electrode and a digital pH meter. A standard fluoride curve was similarly prepared as a control. The mv values obtained on the samples were compared to the control.

Examples 1-2

These examples were made in the following manner with the components and their respective amounts listed in Table 1.

The components in phase A were mixed in a Hobart mixer until the CMC 7MXF (carboxymethylcelluose, available from Hercules Incorporated, Aqualon Division, Hercules Plaza (Wilmington, Del.)) was dispersed in the glycerin. Then, the ingredient in phase B with half of the amount of water were mixed together in a separate mixing container and heated to 55° C. to better dissolve the components prior to adding phase B to phase A. The other half of the water was used to rinse the container holding phase B materials into phase A.

The Zeodents (hydrated silicas, both available from J. M. Huber Corporation, Edison, N.J.), were extensively mixed until dispersed in the combination of phase A and B. When Pluronic P84 (an ethylene oxide/propylene oxide copolymer available from BASF Corporation, New Jersey), a foaming agent was added, the mixture thickened dramatically.

Then, the flavoring and surfactant in phase D were added to the thickened dispersion with moderate mixing until dispersed. Finally, Timica Extralarge Sparkle 110S (titanium dioxide/mica, available from Engelhard Corporation, Iselin, N.J.) was added and mixed under vacuum to remove all air/foam.

Fluoride efficacy was tested by the Oral Health Research Institute at the University of Indiana (Indianapolis, Ind.) and the results are reported in Table 2.

TABLE 1

|  | Example 1 | | | Example 2 | | |
| --- | --- | --- | --- | --- | --- | --- |
|  | % | Batch (g) | Order | % | Batch (g) | Order |
| Phase A |  |  |  |  |  |  |
| Glycerin | 7 | 21 | 1 | 8.25 | 24.75 | 1 |
| CMC 7MXF | 0.8 | 2.4 | 1 | 0.8 | 2.4 | 1 |
| Phase B |  |  |  |  |  |  |
| Water | 15 | 45 | 2 | 15 | 45 | 2 |
| Sorbitol (70% soln) | 34.37 | 103.11 | 2 | 34.37 | 103.11 | 2 |
| Xylitol C | 2.1 | 6.3 | 2 | 2.1 | 6.3 | 2 |
| Acesulfame | 0 | 0 | 2 | 0 | 0 | 2 |
| Na Saccharin | 0.25 | 0.75 | 2 | 0.25 | 0.75 | 2 |
| Na F | 1.13 | 3.39 | 2 | 1.13 | 3.39 | 2 |
| KNO3 | 5 | 15 | 2 | 2.5 | 7.5 | 2 |
| FD & C Blue #1 (1% sol'n) | 0.4 | 1.2 | 2 | 0.4 | 1..2 | 2 |
| D&C yellow #10 (1% sol'n) | 0.2 | 0.6 | 2 | 0.2 | 0.6 | 2 |
| Water | 10 | 30 | 2 | 10 | 30 | 2 |
| Phase C |  |  |  |  |  |  |
| Zeodent 215 | 15 | 45 | 3 | 16.25 | 48.75 | 3 |
| Zeodent 165 | 6 | 18 | 3 | 6 | 18 | 3 |
| Pluronic | 0.5 | 1.5 | 3 | 0.5 | 1.5 | 3 |
| Phase D |  |  |  |  |  |  |
| Flavor | 0.8 | 2.4 | 4 | 0.8 | 2.4 | 4 |
| Sodium Laurel Sulfate | 1.2 | 3.6 | 4 | 1.2 | 3.6 | 4 |
| Timica Extralarge Sparkle 110S | 0.25 | 0.75 | 5 | 0.25 | 0.75 | 5 |
| Total | 100 | 300 |  | 100 | 300 |  |

TABLE 2

| Example | Total Fluoride (ppm) | Available Fluoride (ppm) |
| --- | --- | --- |
| 1 | 5364 ± 33 | 4932 ± 33 |
| 2 | 5362 ± 33 | 5049 ± 33 |

Having described the invention with reference to accompanying illustrations and examples of the invention, it is contemplated that other changes may be made without departing from the spirit or scope of the invention as set forth in the appended claims.

What is claimed is:

1. A one-component fluoride dentifrice gel or paste comprising:
   at least one metal fluoride comprising from about 4900 ppm to about 5000 ppm of available fluoride;
   up to less than about 5 percent by weight of the composition of at least one de-sensitizing agent selected from the group consisting of alkali nitrates, potassium carbonates, potassium chloride and mixtures thereof; and
   about 0.2 percent to about 2 percent by weight of at least one source of sodium or potassium phosphate;
   wherein the amount of said available fluoride of said gel or paste remains stable for 90 days at 37° C.

2. The one-component fluoride dentifrice of claim 1 wherein said metal fluoride is sodium fluoride.

3. The one-component fluoride dentifrice of claim 1 wherein said metal fluoride comprises up to about 1.15% by weight of the composition.

4. The one-component fluoride dentifrice of claim 1 wherein the composition comprises a total fluoride content of at least about 5,000 ppm to about 5,300 ppm.

5. The one-component fluoride dentifrice of claim 1 further comprising at least one ingredient selected from the group consisting of abrasives, thickeners, binders, surfactants, foaming agents, water, sweeteners, preservatives, vitamins, flavorings, coloring agents, anti-plaque agents, anti-staining compounds, and pH adjusting agents.

6. The one-component fluoride dentifrice of claim 5 wherein said abrasive component is selected from a group consisting of silicas and hydrates thereof; alumina and hydrates thereof; silicates; aluminosilicate; carbonates; polymethylmethacrylate; powdered polyethylene; silica xerogels, hydrogels, aerogels; calcium pyrophosphate; insoluble sodium metaphosphate; dicalcium orthophosphate; particulate hydroxyapatite and mixtures thereof.

7. A one-component dentifrice gel or paste comprising:
   less than about 1.15% by weight of the composition of at least one metal fluoride;
   less than about 5 percent by weight of the composition of at least one alkali nitrate;
   at least one carrier; and
   at least one foaming agent which is also a thickening agent;
   wherein said gel or paste provides an available fluoride amount of at least about 4,800 to about 5,000 ppm, and said available fluoride amount remains stable after 90 days at 37° C.

8. The one-component dentifrice of claim 7 further comprising at least one ingredient selected from the group consisting of abrasives, thickeners, binders, surfactants, foaming agents, water, sweeteners, preservatives, vitamins, flavorings, coloring agents, anti-plaque agents, anti-staining agents and pH adjusting agents.

9. The one-component dentifrice of claim 8 further comprising an effective amount of at least one source of sodium or potassium phosphate without impeding the available fluoride amount.

10. The one-component dentifrice of claim 8 wherein said water content is at a level of about 37% by weight of the composition.

11. The one-component dentifrice of claim 7 wherein said carrier comprises a polyol.

12. The one-component dentifrice of claim 7 wherein said carrier comprises a non-ionic surfactant, an anionic surfactant or combinations thereof.

13. The one-component dentifrice of claim 6 wherein said surfactant comprises a non-ionic surfactant, an anionic surfactant or combinations thereof.

14. The one-component dentifrice of claim 7 wherein said at least one alkali nitrate is potassium nitrate potassium nitrate.

15. A one-component fluoride treatment gel or paste composition comprising:
   from about 1 to about 1.15 percent by weight of the composition of at least one metal fluoride;
   from about 3 to about 5 percent by weight of the composition of at least one non-fluoride metal salt having desensitizing effect; and
   at least one carrier comprising water at a level of about 37% by weight of the composition;
   wherein said gel or paste provides an available fluoride amount of from about 4,800 to about 5,000 ppm, the amount of said available fluoride remains stable for 90 days at 37° C.

16. The one-component fluoride treatment composition of claim 15 further comprising at least one ingredient selected from the group consisting of abrasives, thickeners, binders, foaming agents, sweeteners, preservatives, vitamins, flavorings, coloring agents, anti-plaque agents, anti-staining compounds, and pH adjusting agents.

17. The one-component fluoride treatment composition of claim 16 wherein said foaming agent comprises hydrophilic and hydrophobic components.

18. The one-component fluoride treatment composition of claim 17 wherein said foaming agent comprises a copolymer of ethylene oxide and propylene oxide.

19. The one-component fluoride treatment composition of claim 16 wherein said surfactant comprises a non-ionic surfactant, an anionic surfactant or combinations thereof.

20. The one-component fluoride treatment composition of claim 15 wherein said metal fluoride is sodium fluoride.

* * * * *